United States Patent [19]

Hastings

[11] 4,009,718
[45] Mar. 1, 1977

[54] EARLOBE PIERCING DEVICE

[76] Inventor: John A. Hastings, 31 Main St., Bass River, Mass. 02664

[22] Filed: Mar. 17, 1975

[21] Appl. No.: 559,034

Related U.S. Application Data

[63] Continuation-in-part of Ser. No. 446,749, Feb. 28, 1974.

[52] U.S. Cl. .............................................. 128/330
[51] Int. Cl.$^2$ ....................................... A61B 17/00
[58] Field of Search .................................... 128/330

[56] References Cited

UNITED STATES PATENTS

| | | | |
|---|---|---|---|
| 3,187,751 | 6/1965 | Coren et al. | 128/330 |
| 3,641,804 | 2/1972 | Oudenhoven | 128/330 X |
| 3,941,134 | 3/1976 | McDonald | 128/330 |
| 3,943,935 | 3/1976 | Cameron | 128/330 |

FOREIGN PATENTS OR APPLICATIONS

| | | | |
|---|---|---|---|
| 242,379 | 12/1962 | Australia | 128/330 |
| 311,925 | 5/1929 | United Kingdom | 128/330 |

Primary Examiner—Channing L. Pace
Attorney, Agent, or Firm—Wolf, Greenfield & Sacks

[57] ABSTRACT

An ear lobe piercing device is employed to drive a headed pin through an ear lobe and into a lock nut disposed on the other side of the ear lobe. In one form the device includes a pair of separable jaws which receive the ear lobe therebetween, one of the jaws having a pin driving mechanism and the other jaw having means for holding the lock nut in a position to receive the sharp end of the pin. Both the pin and nut are individually pre-packaged, each in its own holder. The pin holder is received by one jaw in alignment with the pin driving mechanism, and the nut holder is received by the other jaw. After insertion of the two holders into the device and operation of the device to pierce the ear lobe, the holders are disposable. The device can also be in the form of a gun having a fixed means for receiving the pin holder and a slidable means for receiving the nut holder.

8 Claims, 22 Drawing Figures

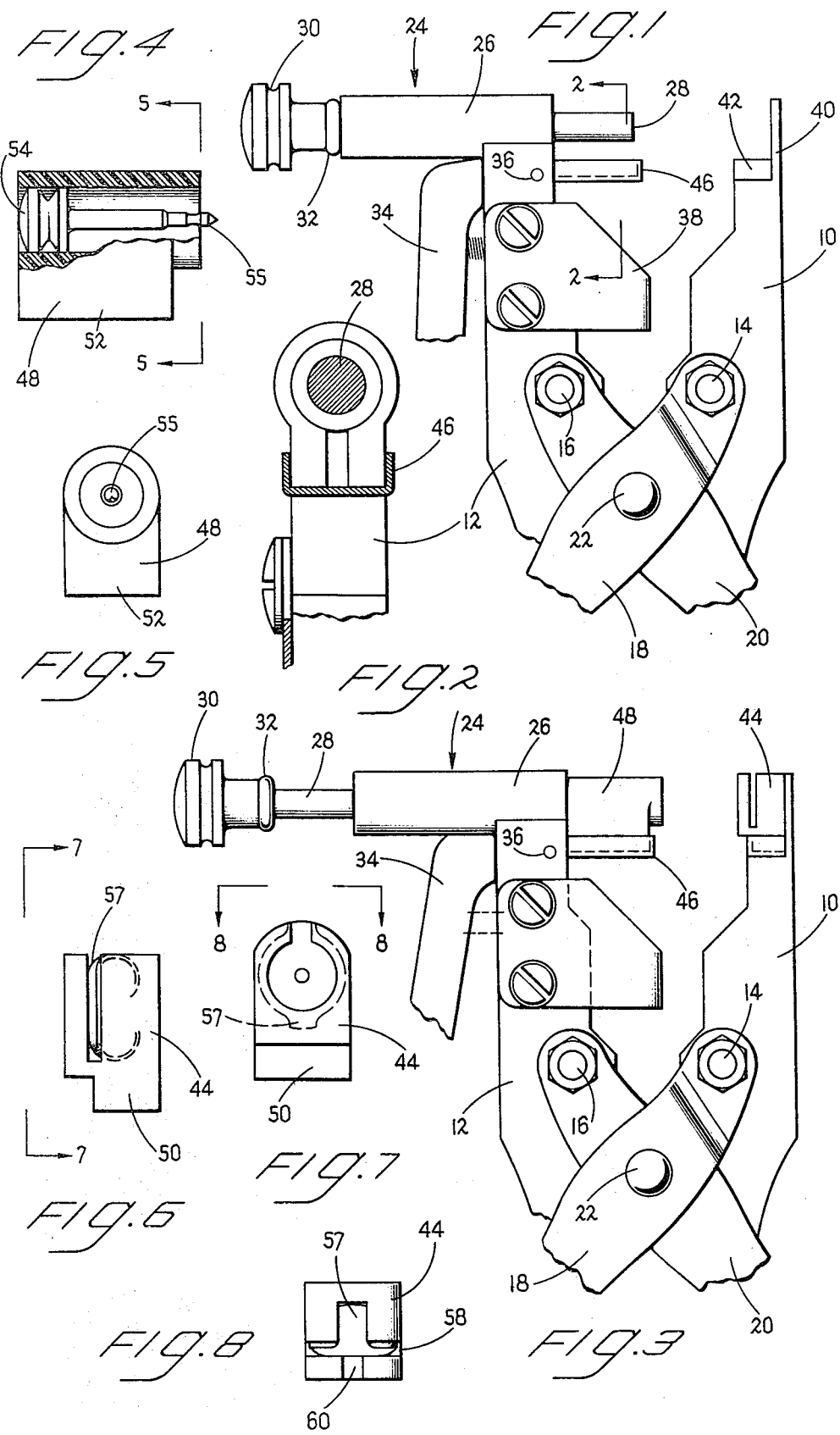

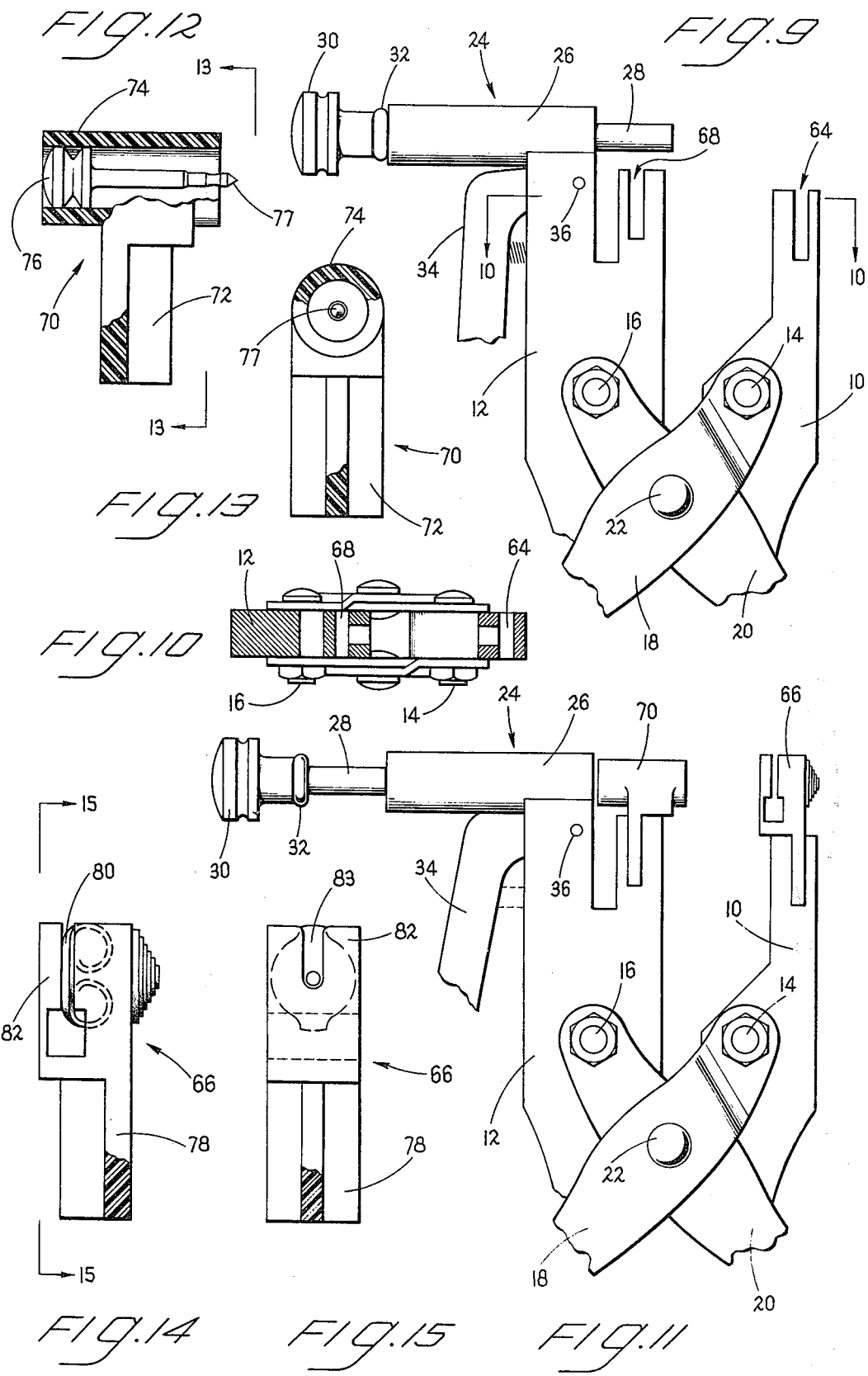

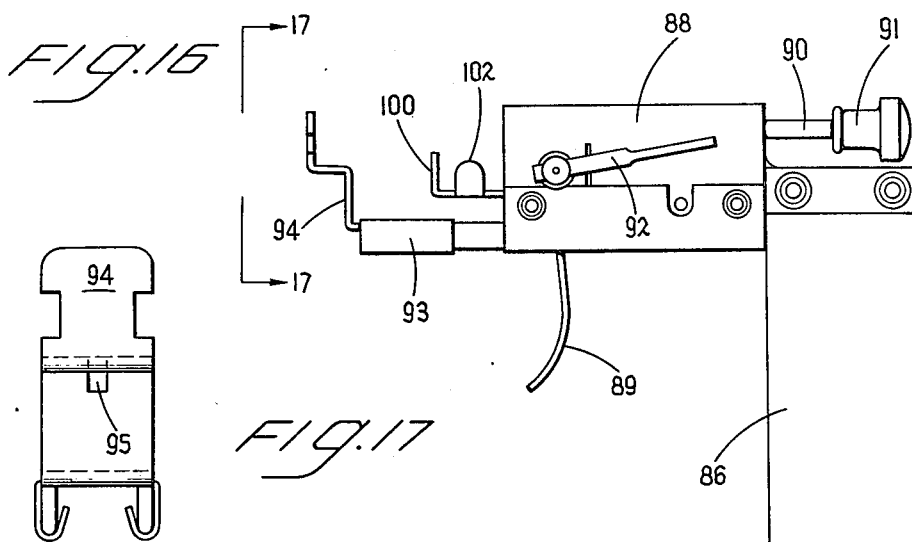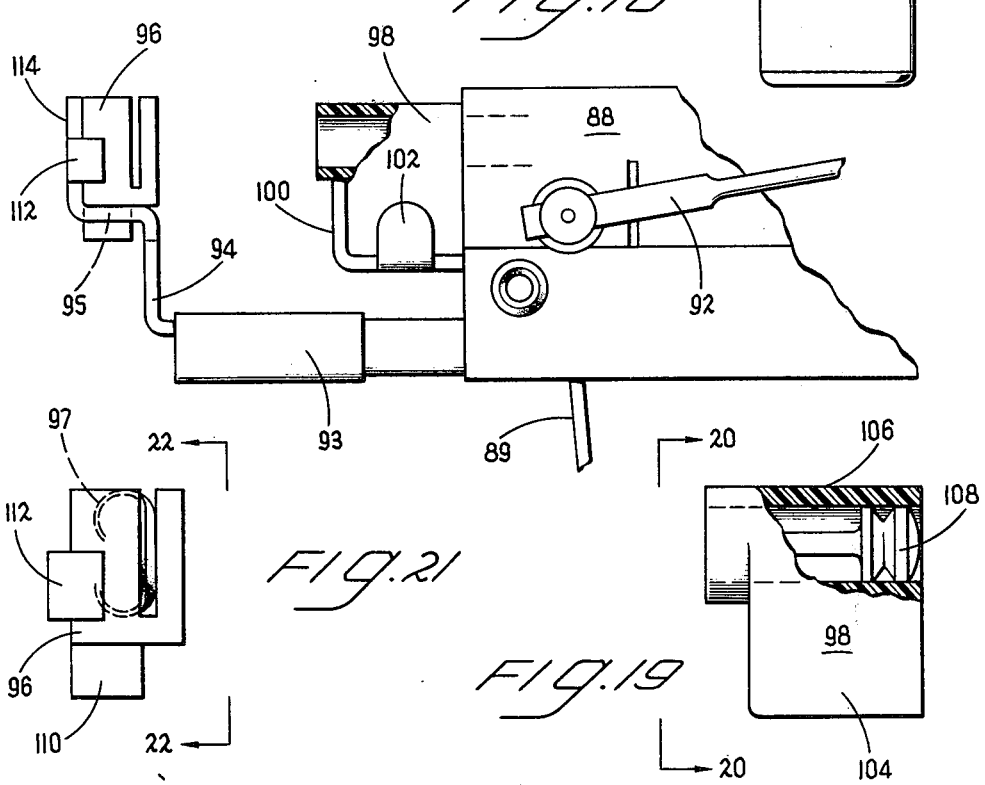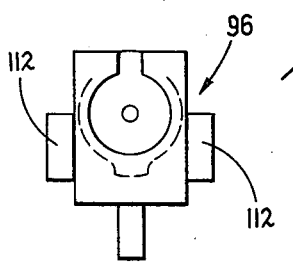

EARLOBE PIERCING DEVICE

RELATED APPLICATION

This is a continuation-in-part of application Ser. No. 446,749 filed Feb. 28, 1974.

BACKGROUND OF THE INVENTION

The present invention relates, in general, to improvements in surgical instruments, particularly those employed for ear lobe piercing operations. More particularly, the present invention relates to an improved ear lobe piercing device of the type having separable members which receive the ear lobe therebetween and which members respectively carry aligned pin and lock nut holders or retainers.

Application Ser. No. 446,749 shows an ear lobe piercing device that is in the form of a pair of pliers having separate jaws for carrying a pin and lock nut, respectively. The operation of this device is quite satisfactory but from the medical standpoint there is a problem in that the pin and nut may become contaminated upon being handled for insertion into the jaws of the device. Even though the piercing of an ear lobe is not a major operation, nonetheless sterile conditions should prevail.

Accordingly, one object of the present invention is to provide an ear lobe piercing device having means for receiving the pin and lock nut in a sterilized condition.

Another object of the present invention is to provide an ear lobe piercing device having respective means for receiving holders for the pin and lock nut, which holders are disposable after use.

SUMMARY OF THE INVENTION

In one form the improved device of the present invention includes a pair of jaws which are movable toward and away from each other, one of the jaws having pin driving means associated therewith and the other jaw including means for receiving and carrying a nut so that as the pin is driven through the ear lobe, the nut receives and engages the end of the pin to lock it in place on the subject's ear lobe. The nut and pin each are maintained in a sterile state by being held each in a holder. The driving means associated with the pin carrying jaw may comprise a spring loaded piston or plunger which is preferably cocked prior to insertion of the pin holder. A lever or trigger is associated with this jaw for releasing the drive means for driving the pin from its holder and toward the other jaw. Of course, this driving operation only takes place when the ear lobe has been inserted between the jaws and the lock nut holder has been inserted or received by the other jaws. Thus, the other jaw includes a chuck that is configured to receive the disposable lock nut holder. This chuck may simply be in the form of a guidewave or it may be slotted to receive the holder.

In another form the device is shaped like a gun having a body with a pin driving means contained therein. A fixed means extends from the body and receives a pin holder with the pin in alignment with the driving means and a slideable means also extends from the body, receives a nut holder and permits movement of the nut holder toward the pin holder when the ear lobe is therebetween.

On important aspect of the present invention is the use of individual holders or retainers for the pin and lock nut respectively. There is disclosed herein different embodiments of these holders wich are usable with different embodiments of the ear piercing device. These holders protect the pin and nut from contamination during handling and after the device is operated to interlock the pin and nut, both holders are disposable.

BRIEF DESCRIPTION OF THE DRAWINGS

Numerous other objects, features and advantages of the invention will now become apparent upon a reading of the following detailed description taken in conjunction with the accompanying drawings, in which:

FIG. 1 is a fragmentary view showing a first embodiment of device of this invention;

FIG. 2 is a cross-sectional view taken along line 2—2 of FIG. 1;

FIG. 3 is a view like that shown in FIG. 1 with the device cocked and the pin and nut holders disposed in the device;

FIG. 4 is a cut-a-way view of the pin holder shown in FIG. 3;

FIG. 5 is a cross-sectional view taken along line 5—5 of FIG. 4;

FIG. 6 is a somewhat enlarged view of the lock nut holder shown in FIG. 3;

FIG. 7 is a view of the holder shown in FIG. 6 as taken along line 7—7 in FIG. 6;

FIG. 8 is a top view of the holder shown in FIG. 7 as taken along line 8—8 of FIG. 7;

FIG. 9 is a fragmentary view similar to that shown in FIG. 1 for a second embodiment of the invention;

FIG. 10 is a cross-sectional view taken along line 10—10 of FIG. 9;

FIG. 11 is a fragmentary view similar to that shown in FIG. 9 with the device cocked and with the pin and lock nut holders disposed in the device;

FIG. 12 is a cut-a-way view showing the pin holder depicted in FIG. 11;

FIG. 13 shows the pin holder of FIG. 12 as viewed along line 13—13 of FIG. 12;

FIG. 14 shows the lock nut holder depicted in FIG. 11;

FIG. 15 is another view of the holder shown in FIG. 14 as viewed along line 15—15 of FIG. 14;

FIG. 16 shows a third embodiment of the present invention in the form of a trigger gun;

FIG. 17 is another view of the device shown in FIG. 16 as seen along line 17—17 of FIG. 16;

FIG. 18 is a somewhat enlarged fragmentary view of the device shown in FIG. 16 with the pin and lock nut holders disposed in the device;

FIG. 19 is a partially cut-a-way view of the pin holder shown in FIG. 18;

FIG. 20 is another view of the pin holder shown in FIG. 19 as viewed along line 20—20 of FIG. 19;

FIG. 21 shows the lock nut holder depicted in FIG. 18; and

FIG. 22 is another view of the lock nut holder shown in FIG. 21 as viewed along line 22—22 of FIG. 21.

DETAILED DESCRIPTION

My co-pending application Ser. No. 446,749 discloses an ear lobe piercing device that is quite similar in structure and operation to the device disclosed in the first two embodiments of the present application. The first two embodiments show a pair of jaws which are movable toward and away from each other to embrace a selected region of the ear lobe and subsequently drive an ear lobe piercing pin through the ear lobe into engagement with a lock nut. In accordance with this invention, the piercing pin and lock nut are each separately contained in a holder and each holder is inserted in a respective jaw of the device. The third embodiment shown herein is in the form of a gun and also has separate pin and lock nut holders or retainers which are disposable after use.

In the first two embodiments of this invention parts that function similarly will be identified by the same reference characters.

Thus, in FIGS. 1-15, there is shown an ear lobe piercing device which includes a pair of jaws 10 and 12 which are movable toward and away from each other by any convenient means. In the illustrative embodiments the jaws 10 and 12 are each pivotally mounted by bolts 14 and 16 to the ends of a pair of crossed handles 18 and 20, respectively, which may be pivoted to each other by a pin 22 intermediate their ends. The arms and jaws are conventionally biased away from each other as shown in FIG. 1, for example, by well known means. See for example, U.S. Pat. No. 3,187,751 which shows a pair of biasing springs for normally biasing the jaws away from each other.

In the first two embodiments disclosed herein there is disposed as the end of jaw 12 a pin driving mechanism 24 which includes a barrel 26 secured to the upper end of the jaw 12. A rod 28 extends through the barrel and has a knob 30 secured at its rearward end. A resilient O-ring 32 may be disposed about the rod 28 between the knob 30 and the barrel 24 to cushion the shock of the driving mechanism.

As depicted in application Ser. No. 446,749 and U.S. Pat. No. 3,187,751, a spring may be disposed in the barrel 26 and the rod 28 may be provided with a detent for receiving a catch of the pivot lever 34. Lever 34 pivots at point 36. In FIGS. 1 and 9 the device is shown in its uncocked position with the rod 28 extending forwardly of the barrel 26. In FIGS. 2 and 11 the driving mechanism is cocked with the lever 34 pivoted for engagement with a detent in the rod 28 against the bias of a spring comprising a part of the driving mechanism contained in the barrel and not shown in the drawings of this application.

In the first embodiment shown herein, depicted in FIGS. 1-8, the relative movement of the jaws 10 and 12 toward each other is limited by means of a stop 38 which is secured to the upper end of jaw 12 and contacts a facing surface of jaw 10. The stop 38 is suitably attached to jaw 12 in any well known manner such as that disclosed in FIG. 1. The second embodiment has a wide jaw 12 which is especially constructed so as to contact jaw 10 and the configuration of the two jaws function as a stop.

In accordance with the present invention and with particular reference now to the first embodiment shown in FIGS. 1-8, the jaw 10 terminates in a vertical upright wall 40 and an open box 42 for receiving the lock nut holder 44. The other jaw 12 has extending from its top end a box shaped extension 46 for receiving the pin holder 48. The holder 44 includes a base 50 received in the box 42 and the holder 48 also includes a base 52 received in the extension 46. FIG. 3 shows both holders in place with the pin driving mechanism 24 in its cocked position.

The holder 48 accommodates a pin 54 having a tip 55. The holder 48 may be constructed of plastic and has an interval passage for accommodating the pin 54.

The pin 54 is preferably held snugly within its holder 48.

The holder 50 is shown with the lock nut 57 disposed therein. The holder 50 has orthogonal slots 58 and 60 for receiving the lock nut 57. FIG. 8 shows the lock nut 57 in a position wherein the tip of the pin 54 can pass through the slot 60 into engagement with the lock nut 57.

In the first embodiment, the first operation is usually to cock the pin driving mechanism 24. Then the holders 44 and 48 may be inserted into the device as shown in FIG. 2. The two jaws are then urged towards each other when the holders are positioned on opposite sides of the ear lobe. When the proper position is obtained then the lever 34 can then be depressed to release the driving mechanism 24 and drive the pin from its holder 48 and into engagement with the locking nut 57. Because the pin has been released from its holder, the holder 48 can now be disposed of and likewise the holder 44 can be disposed of by separating the holder 44 from its lock nut 57.

The embodiment shown in FIGS. 9-15 depicts another means for inserting the pin and lock nut holders into the device. As depicted in FIGS. 9 and 10, the jaw 10 terminates at its top end in a series of posts forming a T-shaped slot 64 for accommodating the lock nut holder 66 shown in position in FIG. 11 with the device in its cocked position. Similarly, the jaw 12 terminates in a series of posts forming another T-shaped slot 68 for accommodating the pin holder 70 shown in position in FIG. 11. The jaws and their respective slots along with the holders 66 and 70 are configured so that the two holders are in line as shown in FIG. 11.

The pin holder 70 is shown in FIGS. 12 and 13 and comprises a T-shaped base 72 for fitting within the T-shaped slot 68. The holder 70 also comprises a barrel 74 for accommodating the conventional pin 76 having its tip 77. The pin 76 preferably is fitted snugly within the barrel 74 of the holder 70. Likewise, the lock nut holder 66 has a T-shaped base 78 which fits within the T-shaped slot 64 in the jaw 10. FIGS. 14 and 15 show the holder 66 with its T-shaped base 78 and its upper portion for retaining the lock nut 80. The upper portion of the holder 66 may have a shape similar to that shown in FIGS. 6-8 and preferably has a flexible wall 82 which permits easy insertion of the lock nut into the holder. FIG. 15 shows a slot 83 in the wall 82 through which the pin passes for engagement with the lock nut.

The embodiment shown in FIGS. 9-15 operates similarly to the operation discussed with reference to FIGS. 1-8. Once the device has been cocked and the holders are fixed in place, then the lever 34 releases the driving mechanism to drive the pin 76 through the ear lobe and into engagement with the lock nut 80 disposed on the other side of the ear lobe.

The third embodiment of this invention is somewhat different than the first two embodiments and is in the form of a gun having a handle 86, a main body 88, and a trigger 89. The main body 88 carries a rod 90 having a handle 91 for pulling the rod away from the body against the bias of a spring (not shown) contained within the body 88. The third embodiment also comprises a lever 92 which is for releasing the rod 90. The cocking arrangement including the lever 92 may be of conventional design with the lever having a biasing means associated therewith and interengaging with the rod 90 to hold the rod in a cocked position such as shown in FIG. 16.

The trigger 89 connects to a plate inside of the body 88 which plate also extends forwardly and terminates in a platform 93. The platform 93 has an angle bracket 94 extending therefrom and as depicted in FIG. 18 the bracket 94 has a slot 95 for receiving the lock nut holder 96. When the trigger 89 is pulled toward the handle 86 the platform 93 and associated bracket 94 are pulled therewith so that the holder 96 and associated lock nut 97 can be more closely positioned to the pin holder 98. To accommodate the holder 98, the device includes a fixed angle platform 100 having side tabs 102. The upturned end of the platform 100 and the tabs 102 define a place for the pin holder 98.

FIGS. 19 and 20 show two separate views of the holder 98 which includes a base 104 fitting between the tabs 102 and a barrel 106 for accommodating the conventional pin 108. FIG. 18 shows the holder 98 in place in the device with the rod 90 in its cocked position.

FIGS. 21 and 22 show the nut holder 96. This holder includes a slot arrangement similar to that shown in the other embodiments and also has a base 110 which fits within the slot 95 as shown in FIG. 18. The holder also includes side arms 112 which extend from the holder and fit about the top upright portion 114 of bracket 94.

In operating the device shown in FIGS. 16–22, the rod 90 is first cocked by pulling rearwardly on the handle 91. This cocks the lever 92 to its operative position. The holders 96 and 98 are then inserted to the position shown in FIG. 18 and the trigger 89 is pulled rearwardly with the holders disposed in the appropriate position on either side of the ear lobe. When the device is properly positioned, the lever 92 can then be depressed to release the rod 90 and the rod engages with the pin 108 within the barrel 106 and urges the pin through the ear lobe and into contact with the lock nut disposed on the other side of the ear lobe. After this operation has taken place, the holders 96 and 98 can be discarded.

Having described a limited number of embodiments of the present invention, it should now become apparent to those skilled in the art that numerous other embodiments and modifications of the ones shown herein should be contemplated as falling within the scope of the present invention. For example, it is expected that there are other types of mechanisms including separable members and a driving member. It is contemplated that the concepts of this invention are applicable also to these other types of structures.

What is claimed is:

1. A device for piercing an earlobe with a pin having a head at one end and a point at the other end and for securing the pin to the earlobe with a nut engaging the pointed end of the pin comprising:
   a first means for supporting the pin,
   a second means for supporting spaced from the first supporting means,
   means supportively interconnecting the first and second supporting means for permitting relative movement therebetween,
   a first disposable holder including an open barrel for slidingly receiving and carrying said pin,
   a second disposable holder for removably receiving and carrying said nut,
   said disposable holders each having base portions shaped to be removably inter-engaged with said first means and second means, respectively,
   said first means including means for removably receiving the first holder,
   and said second means including means for removably receiving the second holder,
   and means supporting said plunger means on said first means independent of said holders for movement of said plunger means into engagement with said pin.

2. A device as set forth in claim 1 including means defining a base for removably receiving the first holder which includes wall means for limiting movement of the first holder in the direction of the second holder.

3. A device as set forth in claim 2 including means defining a base for removably receiving the second holder which includes wall means for limiting movement of the second holder in a direction opposite to the first holder.

4. A device as set forth in claim 3 wherein the wall means of the first means defines with the base a box for receiving the first holder.

5. A device as set forth in claim 4 wherein said first holder includes a base for fitting in the box and for supporting the barrel which is open at both ends.

6. A device as set forth in claim 3 wherein the wall means of the second means includes an upright wall extending from the base and side walls defining a box for receiving the second holder.

7. A device as set forth in claim 3 wherein the wall means of the second means includes a pair of upright walls forming a slot, said second holder having a base for fitting in the slot.

8. In combination attachments for use with an earlobe piercing instrument comprising a pair of plastic supports with one support carrying an earlobe piercing pin and the other carrying a nut dimensioned to receive the pin,
   said supports each having base portions shaped to be removably inter-engaged with an earlobe piercing instrument,
   said instrument having a pair of jaws for removably engaging said supports with said pin and nut aligned, and plunger means, means supporting said plunger means on said instrument independent of said supports for movement of said plunger into engagement with said pin.

\* \* \* \* \*